(12) United States Patent
Rich (10) Patent No.: US 7,900,380 B2
(45) Date of Patent: Mar. 8, 2011

(54) USER MOLDABLE ADJUSTABLE INSERT

(75) Inventor: Jeffrey S. Rich, Forest Hills, NY (US)

(73) Assignee: Masterfit Enterprises Inc., Briarcliff Manor, NY (US)

( * ) Notice: Subject to any disclaimer, the term of this patent is extended or adjusted under 35 U.S.C. 154(b) by 1515 days.

(21) Appl. No.: 11/250,143

(22) Filed: Oct. 13, 2005

(65) Prior Publication Data

US 2007/0084084 A1    Apr. 19, 2007

(51) Int. Cl.
  *A43B 13/38* (2006.01)
  *A43B 13/40* (2006.01)
  *A43B 7/28* (2006.01)

(52) U.S. Cl. .................................. 36/154; 36/44; 36/155

(58) Field of Classification Search ................ 36/43, 44, 36/153, 154, 155
See application file for complete search history.

(56) References Cited

U.S. PATENT DOCUMENTS

| | | | |
|---|---|---|---|
| 2,794,270 A * | 6/1957 | Dubner | 36/93 |
| 3,777,419 A * | 12/1973 | Nalick | 36/71 |
| 4,211,236 A * | 7/1980 | Krinsky | 36/153 |
| 4,580,356 A * | 4/1986 | David | 36/43 |
| 4,603,493 A | 8/1986 | Eston | |
| 4,633,877 A | 1/1987 | Pendergast | |
| 4,716,662 A | 1/1988 | Bar | |
| 4,718,179 A * | 1/1988 | Brown | 36/44 |
| 4,813,157 A | 3/1989 | Boisvert et al. | |
| 5,003,708 A | 4/1991 | Daley | |
| 5,184,409 A | 2/1993 | Brown | |
| 5,203,793 A | 4/1993 | Lyden | |
| 5,345,701 A | 9/1994 | Smith | |
| 5,394,626 A | 3/1995 | Brown | |
| 5,400,528 A | 3/1995 | Skinner et al. | |
| 5,488,786 A | 2/1996 | Ratay | |
| 5,611,153 A | 3/1997 | Fisher et al. | |
| 5,632,057 A | 5/1997 | Lyden | |
| 5,722,186 A | 3/1998 | Brown | |
| 5,732,481 A | 3/1998 | Farhad | |
| 5,733,647 A | 3/1998 | Moore, III et al. | |
| 5,768,803 A | 6/1998 | Levy | |
| 5,996,254 A | 12/1999 | Goven | |
| 6,000,147 A | 12/1999 | Kellerman | |
| 6,003,250 A | 12/1999 | Cheong | |
| 6,025,414 A * | 2/2000 | Rich | 523/167 |
| 6,026,595 A * | 2/2000 | Curry | 36/93 |
| 6,038,793 A | 3/2000 | Kendall | |
| 6,105,283 A | 8/2000 | Park | |
| 6,125,557 A * | 10/2000 | Brown | 36/144 |

(Continued)

*Primary Examiner* — Mickey Yu
*Assistant Examiner* — Sharon M Prange
(74) *Attorney, Agent, or Firm* — Theobald Dengler; McGlew and Tuttle, P.C.

(57) ABSTRACT

An insole which is individually adaptable for insertion in footwear is disclosed. The insole has an upper cradle having an upper surface for contact with a foot. The upper surface is a ETC material. A lower interlocking surface is molded of EVA for cushioning of the foot. A lower cradle having an upper surface with an arch depression and a lower surface with flow domes provided. The flow dome has a flow hole fluidly communicating with the arch depression. A gel layer is placed in the arch depression, the gel layer being moldable via heat. The insole is heated to allow the gel layer to soften. The user then places their foot in on the insole allowing the gel layer to conform to the user's feet. The gel layer then cools and sets in the shape. Excess gel in the gel layer runs out through the flow holes and fills the flow domes. The excess gel is removed and the flow dome is plugged.

23 Claims, 11 Drawing Sheets

U.S. PATENT DOCUMENTS

| | | |
|---|---|---|
| 6,138,383 A | 10/2000 | Steinke et al. |
| 6,205,685 B1 | 3/2001 | Kellerman |
| 6,238,359 B1 | 5/2001 | Anderson |
| 6,280,815 B1 | 8/2001 | Ersfeld et al. |
| 6,301,805 B1 | 10/2001 | Howlett et al. |
| 6,345,455 B1 | 2/2002 | Greer, Jr. et al. |
| 6,412,194 B1 | 7/2002 | Carlson et al. |
| 6,453,578 B1 * | 9/2002 | Yung et al. ............ 36/43 |
| 6,598,319 B2 | 7/2003 | Hardt |
| 6,609,314 B1 | 8/2003 | Dubner |
| 6,631,568 B2 | 10/2003 | Howlett et al. |
| 6,681,501 B1 | 1/2004 | Polifroni |
| 6,782,640 B2 | 8/2004 | Westin |
| 6,804,902 B1 | 10/2004 | McCracken et al. |
| 7,020,990 B2 * | 4/2006 | Khoury ................ 36/154 |
| 7,062,866 B2 * | 6/2006 | Bussler .................. 36/34 R |
| 7,257,907 B2 * | 8/2007 | Green .................... 36/93 |
| 2001/0049026 A1 | 12/2001 | Snow |
| 2002/0007568 A1 | 1/2002 | Kellerman et al. |
| 2002/0092203 A1 | 7/2002 | Hardt |
| 2003/0061736 A1 | 4/2003 | Polifroni |
| 2003/0061738 A1 | 4/2003 | Grohninger |
| 2003/0088999 A1 | 5/2003 | Ailey et al. |
| 2004/0003514 A1 | 1/2004 | Cole |
| 2004/0005599 A1 | 1/2004 | Schoenbrunner et al. |
| 2004/0103558 A1 | 6/2004 | Everz |
| 2004/0181971 A1 | 9/2004 | Turkbas et al. |
| 2004/0194344 A1 | 10/2004 | Tadin |
| 2004/0194348 A1 | 10/2004 | Campbell et al. |

* cited by examiner

USER MOLDABLE ADJUSTABLE INSERT

FIELD OF INVENTION

This invention relates to orthopedic inserts and more specifically, to a user moldable insert insole that may be modified for an individual user's foot.

BACKGROUND OF INVENTION

Currently, there are various mechanisms which offer varying degrees of support and control of the foot. Insoles such as arch supports, custom footbed and orthotics have been known for years. Such insoles are designed to alleviate foot problems, provide comfort and give better performance. The insole not only supports the foot but the whole body aligning joints in the foot, knee, hip and back while molding to the exact contours of the arch. Some inserts are off-the-shelf and those cannot be adjusted to an individual user's foot, others are semi-custom formed taking a partial mold or only adjusting to the foot slightly.

Most insoles attempt to support the foot but because of the various foot arch heights, cannot offer a lot of arch support. Most insoles are made with a lower arch height because if the arch were too high, many individuals would find it uncomfortable. A high arch can create excessive pressure under the arch yielding a very uncomfortable fit. Often the excessive arch height can cause foot cramping or injury. Most over-the-counter insoles have very low heel cups and medial and lateral flanges that do not adequately secure the heel or control the foot. They also offer little or no arch support. Over the counter insoles are made via injection molding, skive molding or compression molding processes. Some these insoles are flat, others have little shape. Still others offer deep heel cups with little or no arch support.

Most semi-custom insoles offer a one-time fit and cannot be adjusted. A few semi-custom and custom insoles offer more arch support but are difficult to manufacture and need adjustments by experienced lab technicians who use a grinder to sand away excess material.

Most semi-custom and over-the-counter insoles are designed for the pronated foot. A pronated foot is one where the ankle rolls inward. Insoles slow down or prevent some pronation from taking effect. A small amount of pronation is considered normal and is needed for shock absorption. Locking up the pronatory effect of the foot with excess arch support or wedging under the heel or forefoot by an untrained user or technician can make the body susceptible to injury.

Other insoles are available with various arch heights or different stiffness but it is up to the user or technician to decide which arch height is best. This provides a potential for harm if either too much or too little support is chosen. This could injure or further injure the foot or body.

Some insoles use compression molding. However, present compression molding methods mold multi-density material of different thickness and material in a one step compression molding process. The drawback for this process is during the compression molding process the softer material is compressed to a very thin state making it useless other than for cosmetic purposes. The one-step compression molding process makes all the multiple layers feel like the same density.

The insoles, which are available, use compression molding. However, present compression molding methods mold multi-density material of different thickness and material in a one step compression molding process. The drawback for this process is compression of the softer material to a very thin state making it useless other than for color. The one-step compression molding process makes all the multi-layers feel like the same material.

Thus, there is a need for an insole that may be adjusted for multiple arch heights. There is a further need for an insole that may be adjusted easily without any error. There is yet another need for an insole that may be used with a normal foot, a pronated foot, a flat foot and a high-supinated foot. There is also a need for an insole that allows flexible heel and forefoot support. There is also a need for a method to manufacture other types of adjustable inserts for other orthopedic applications.

SUMMARY OF THE INVENTION

These needs and others may be met by the present invention of which one example is an insole for insertion in footwear. The insole has an upper cradle which has an upper surface for contact with a foot and a lower interlocking surface. A lower cradle has an upper surface with an arch depression and a lower surface with a flow dome having a flow hole fluidly communicating with the arch depression. A gel layer is located in the arch depression. The gel layer is moldable via heating.

Another example of the present invention is a method of fabricating a corrective insole. A first female mold is provided to produce a lower cradle with an arch depression and a bottom surface with flow domes. A first male mold is provided to produce a different density area of the lower cradle. A second male mold is provided to produce an upper cradle. A gel layer which is heat moldable is inserted in the arch depression of the lower cradle. The upper and lower cradles are attached together.

It is to be understood that both the foregoing general description and the following detailed description are not limiting but are intended to provide further explanation of the invention claimed. The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF DRAWINGS

These and further aspects and advantages of the invention will be discussed more in detail hereinafter with reference to the disclosure of preferred embodiments, and in particular with reference to the appended Figures wherein.

DESCRIPTION OF THE PREFERRED EMBODIMENT

While the present invention is capable of embodiment in various forms, there is shown in the drawings and will hereinafter be described a presently preferred embodiment with the understanding that the present disclosure is to be considered as an exemplification of the invention, and is not intended to limit the invention to the specific embodiment illustrated.

Figure 1:
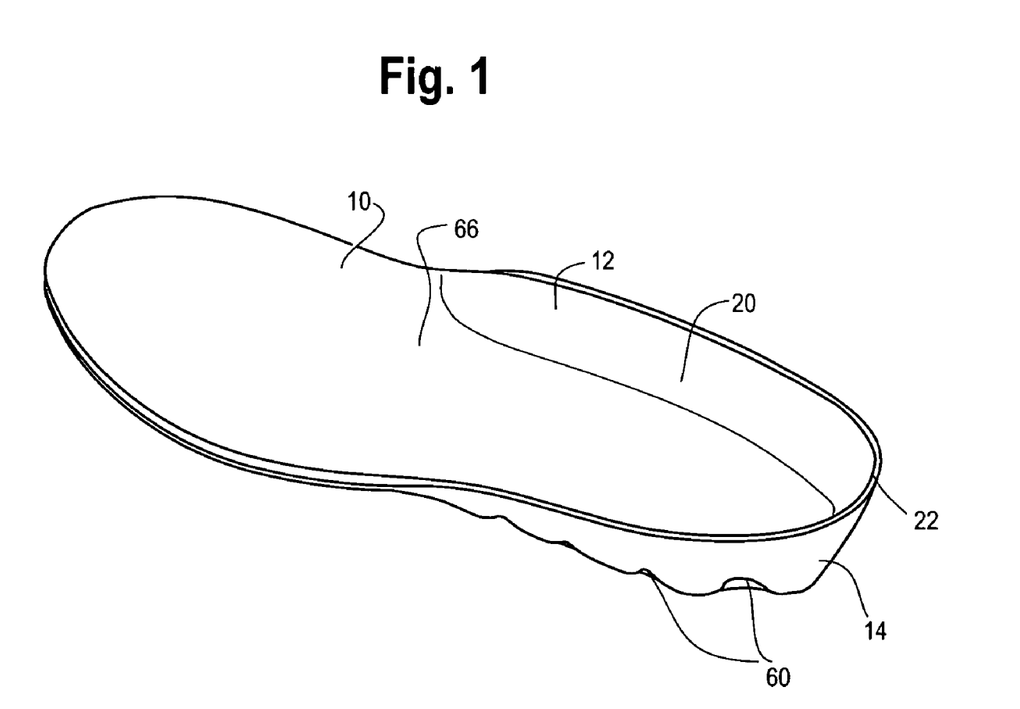
FIG. 1 is a top perspective view of a user moldable insole according to the present invention.
Figure 2:
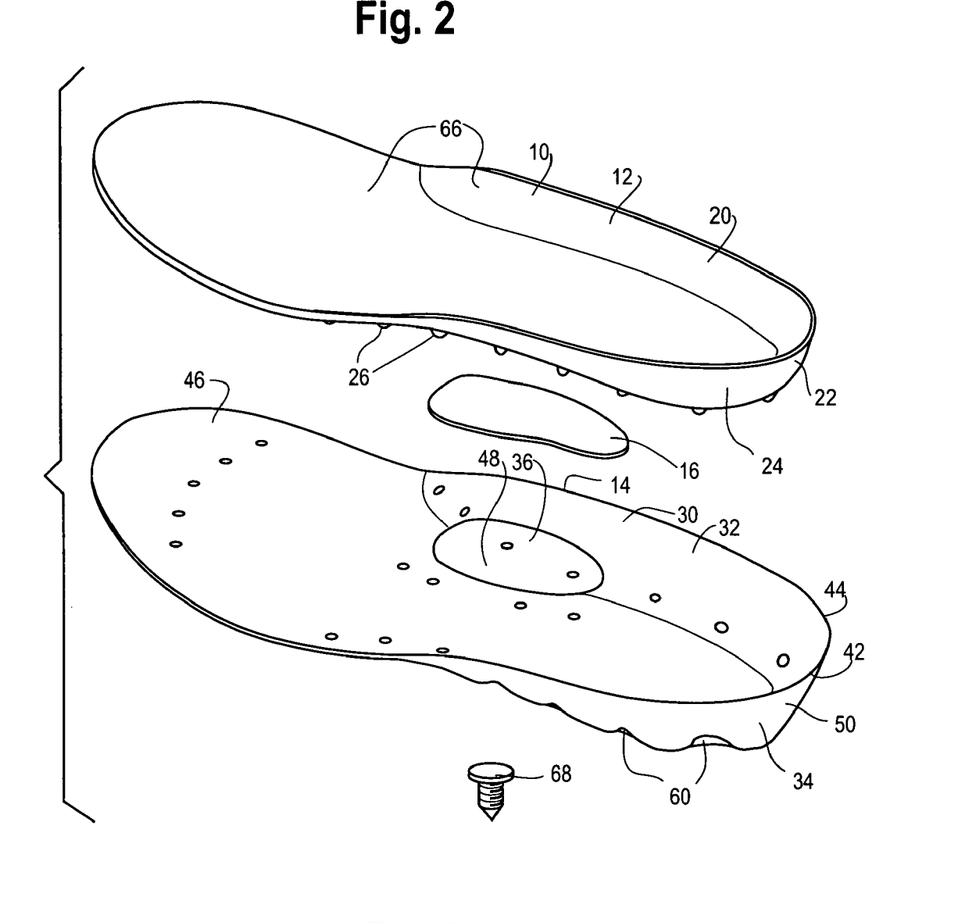
FIG. 2 is an exploded perspective view of the components of the user moldable insole in FIG. 1.

FIG. 1 is a perspective view of an insole 10 according to an embodiment of the present invention. FIG. 2 shows an exploded view of the components of the insole 10. The insole 10 has an upper cradle 12, a lower cradle 14 and a gel layer 16 and is insertable in footwear such as shoes and braces to provide support for a user's foot.

The upper cradle 12 has a top or outer layer 20 which is friction-reducing, moisture-absorbing fabric made of a polyester which is preferably ETC material manufactured by Sheehan Sales of Salem, Mass. upon which the user's foot rests. The material of the top layer 20 wicks away moisture while reducing odor. The material also reduces friction and thus prevents blistering. A cushioned layer 22 is bonded to the top layer 20. Preferably, the cushioned layer 22 is fabricated from ethyl vinyl acetate (EVA). The cushioned layer 22 is preferably ¼" 25 durometer (Shore A scale) before compression molding and 35 durometer ⅛" thick, Shore A scale after molding. The cushioned layer 22 is designed to provide comfort and cushioning. In addition, the cushioned layer 22 will auto-adapt, self adjusting to the wearer's feet and forming toe crests. The cushioned layer 22 also has a lower or inner surface 24 having stubs 26 which interlock the upper cradle 12 with the lower cradle 14. The inner surface 24 being considered inner in the sense of when the upper cradle 12 is combined with the lower cradle 14. Other material may be used for the top layer 20 such as Tricot, vinyl, leather, cambrelle, EVA and other like materials.

Figure 3:
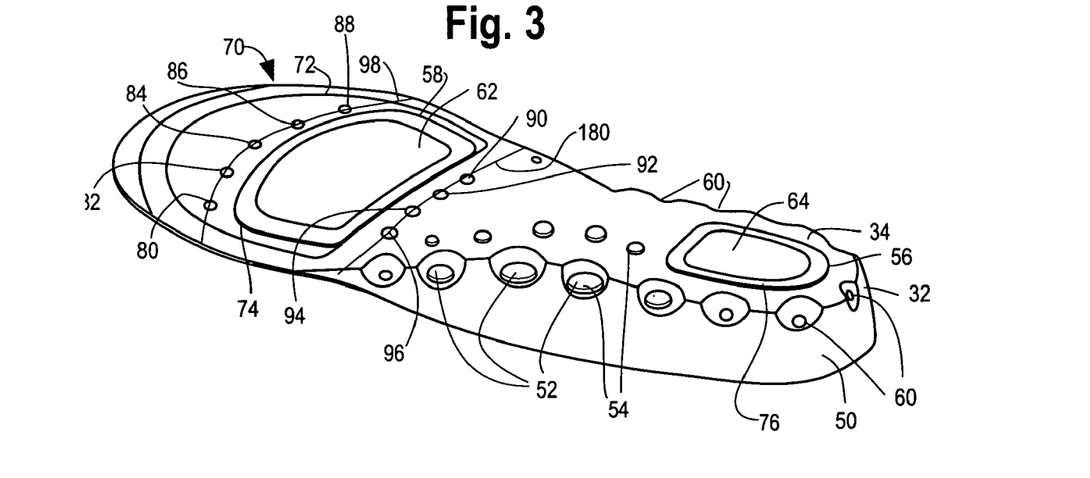
FIG. 3 is a perspective view of the bottom surface of the bottom cradle of the user moldable insole in FIG. 1.

The lower cradle 14, which is bonded to the upper cradle 12, includes an interlocking cradle support or inner surface 30 with a firmer lower core shell 32 which has a bottom or outer surface 34 as may be seen in FIG. 3. The inner surface 30 is inner with respect to the combination of the upper cradle 12 and the lower cradle 14. The lower cradle 14 is fabricated from a single density EVA material but due to compression molding, as will be explained below, has varied density in different areas and is thus multi-density. In this example, the lower cradle 14 before compression molding is a ½" 40D EVA. The lower cradle 14 has various depressions molded into the cradle support 30. One of these depressions is an arch depression or cavity 36 for holding the gel arch layer 16. Other depressions are heel depression 56 and a forefoot depression 58 molded into bottom surface 34 of the lower core shell 32 as shown in FIG. 3. The heel depression 58 has a deep heel cup 42 with an upper rim 44. The cradle support 30 also has a forefoot area 46, an arch area 48, an outside perimeter region 50, a metatarsal area 74 and a heel area 76.

In this example, after compression molding the cradle support 30, the forefoot area 46 is between 75-80 durometer (D) and the arch area 48 is between 45-50 D. The upper rim 44 of the heel cup 42 is between 75-80 D while the base of the heel cup 42 and the outside perimeter region 50 is between 50-55 D. These differing hardnesses give the insole 10 torsional rigidity with easy flexing forefoot. The firm forefoot area 46, medial and lateral arch area 48 and heel rim 44 adds firm control and torsional rigidity (75-80 D) with the arch area 48.

A number of volume compensation domes 60 are molded into the perimeter of the bottom surface 34 of the lower core shell 32 to allow the insole 10 to auto-contour to any shape heel from narrow to wide. Additionally a number of flow domes 52 are molded into the arch of the bottom surface 34 of the lower core shell 32 as shown in FIG. 3. Each of the flow domes 52 have a flow hole 54 which is bored through the lower core shell 32 and cradle support 30 to contact the gel layer 16. The flow domes 52 allow excess gel to exhaust into the flow domes 52 enabling the gel to mold to the individual arch shape. The volume compensating domes 60 are located around the perimeter of the heel depression 56 and lateral side of the foot. The volume compensating domes 60 allow the insole 10 to auto adjust for wide heels or flatter feet.

Additional anti-shock platforms in the form of toe and heel depressions 56 and 58 are molded into the bottom surface 34 of the core support shell 32 making the EVA paper-thin below the metatarsals area 74 and the heel area 76. The toe and heel depressions 56 and 58 allow softer Poron forefoot and heel plugs 62 and 64 to be installed which may be accessed or felt by the foot. In this example, the Poron plugs are ¹⁄₁₆ of an inch thick, but other thicknesses and materials may be used. The EVA material is preferably thin in the depressions 56 and 58 to allow paper like flexibility. The Poron forefoot and heel plugs 62 and 64 are added after compression molding to the toe and heel depressions 56 and 58. Poron is a performance urethane material which provides excellent shock absorption during heel strike and toe-off when jumping, running, walking and other activities to help prevent foot fatigue. Other materials may be used instead of Poron such as sorbathane, EVA of a softer durometer rating, foam, rubber, rigid or flexible plastics or other components to achieve different levels of shock absorption.

The gel layer 16 is sandwiched between the upper cradle 12 and the lower cradle 14 and rests in the arch depression 36 of the lower cradle 14. The upper cradle 12 and the lower cradle 14 are formed of EVA with different densities. As explained above, the lower density EVA in the upper cradle 12 provides cushioning for the foot while the high density EVA in the lower cradle 14 provides support and rigidity. The gel layer 16 permits an arch area 66 formed by the upper and lower cradles 12 and 14 to contour precisely to the natural shape of the user's arch. Preferably the gel material of the gel layer 16 is a heat moldable composition such as Gel Form manufactured by Masterfit Enterprises of Briarcliff Manor, N.Y. according to U.S. Pat. No. 6,025,414 to the same inventor.

When heated to a temperature of 125-140 degrees F., the gel material in the gel layer 16 turns viscous. When weight or pressure is applied to the insole 10, the gel in the gel layer 16 not needed to support the individual arch shape bleeds or exhausts into the flow domes 52 in the lower cradle 14 via the flow holes 54. This supports the arch, stabilizing the foot dramatically and reducing foot, knee and pack pain. The gel layer 16 compensates for various low to high arch heights. For a high arch, the gel of the gel layer 16 will not exhaust into the flow domes 52 because relatively little pressure will be placed on the gel layer 16. For a low arch, all the gel in the gel layer 16 may exhaust into the flow domes 52. The flow domes 52 allow the gel to escape, precisely molding the arch area 66 to the user's arch, yielding a comfortable feel that is not excessively high or tight. Gel that bleeds into the flow dome 52 is removed by hand when cooled and the flow holes 54 in the flow domes 52 are plugged with plastic tree rivets 68 to prevent additional flow of the gel when subject to extreme temperatures within the shoe. Of course, other kinds of plugs may be used. The plastic tree rivets 68 are not need when the insole 10 is used in winter or cold weather environments.

The flow domes 52 thus act as a self-volume compensator allowing the gel to escape if there is too much pressure. The flow domes 52 allow the gel to readily flow and serve as a reservoir for excess gel. Different sizes of the insole 10 can use different amounts of gel layer 16 to allow the arch to precisely mold to various size feet for the individual arch shape and height. The volume of gel may be increased or restored by a technician using a syringe filled with gel warmed to 200-250 degrees F. and injected back thru one or more of the flow domes 52.

The insole 10 is made adaptable for individual user's feet via the following process. First, the user adjusts the length and toe shape of the insole 10 by cutting the proper shape with scissors or another convenient instrument. Grinding or adjusting the insole 10 is not needed in most cases but the corrections and the interlocking cradles 12 and 14 may be adjusted with most any grinder in the event a technician or user wants to perform further customization. All corrections may be made to the EVA, polyurethane, Poron or other hard or soft material in the cradles 12 and 14.

Before heating the insole 10, the insole 10 may be fit into the footwear intended for use. The insole 10 allows for trimming the toe length and width. To make this easier, the toe area 46 of the bottom surface 34 has two embossed marks 70 and 72 for trimming the length and width of the insole 10 as shown in FIG. 3. The sole 10 may remain untrimmed for fitting into sport shoes such as sneakers, golf, running or hiking shoes. The first trim line 70 is for fitting the insole 10 into snowboard boots. The second trim line 72 is for fitting the insole 10 into ski boots. Of course other trim lines may be fabricated to fit the insole 10 into other types of footwear.

The insole 10 and in particular the gel layer 16 is next heated. The preferred method of heating the gel layer 16 for custom molding is a microwave oven with a turntable. The required heating time for the insole 10 depends on five parameters: air, liquid, fat, size and/or thickness of product. Preferably the microwave oven is used at a power of 800-850 watts at full power preferably less than 180 seconds and more preferably 120 seconds. Microwaves having power of 900 watts or more are used preferably less than 90 seconds and more preferably at 60 seconds and optimally at 45 seconds. One gel layer 16 and insole 10 are heated at a time on foam blocks placed beneath the toe and heel to insulate the insole from heat generated by the turntable.

The insole 10 is placed in the microwave with the bottom surface 34 up allowing the flow domes 52 to be facing up. This prevents the gel in the gel layer 16 from oozing out in the event of overheating. Another method of heating the insole 10 is using a hot water bath water for 15 minutes. The insole 10 is turned over midway during the heating cycle to ensure even heating of the gel layer 16. The insole 10 must be placed in a sealed water proof bag. Using a hot water bath heats the gel layer 16 more consistently, the material softens at a predetermined temperature. Heating the insole 10 in microwaves and convection ovens are less consistent because it is more difficult to accurately control temperature. The hot water bath must be between 140-160 degrees F. With hot water, multiple insoles can be heated at one time and be instantly ready for potential fitting without the risk of overheat the insole 10.

The gel molding temperature is 135 degrees F. and thus 140 degrees F. water is hot enough to effect a molding change in the gel without affecting the EVA or other components in the insole 10. The low temperature also prevents skin burns in the event of a mishap.

After the user heats the insole 10 in order to insure that the gel layer 16 becomes viscous, the user inserts the insole 10 into the desired footwear or brace and places their foot on the insole or body part on the brace. The user is in a seated, semi weight-bearing position. The user then stands or walks in the footwear the insole 10 is to be utilized causing the gel layer 16 to conform to the contours of the user's foot. The gel in the gel layer 16 cools in approximately two to four minutes depending on outside air temperature and sets in the shape. The finish-molded insole 10 is transferable to like footwear with removable insoles in them or footwear that is slightly oversized. The excess gel in the gel layer 16 will flow out of the volume flow domes 52 via the flow holes 54 and form gel plugs. These plugs are cut or pulled away and the plastic tree rivets 68 are inserted in the flow domes 52.

Returning to FIG. 3, the bottom surface 34 of the lower cradle 14 has a series of forefoot alignment dots 80-88 and midfoot alignment dots 90-96. The forefoot dots 80-88 when connected along a line 98 to form the outline of the sulcus of the foot, the crest or furrow under and behind the toe pads. This is also where the insole 10 can be cut to at a ⅞ length for toes that need extra room. The forefoot dots 80-88 when connected form the ending point for making a suitable length for dress shoes. The forefoot dots 80-88 and the midfoot dots 90-96 are positioned so when forefoot dots 80-88 and midfoot dots 90-96 are connected front to back, the lines are positioned between the bones of the metatarsal bones in the foot. The dot 80 connects to dot 96, the dot 84 connects to dot 94, the dot 86 connects to dot 92 and the dot 88 connects to dot 90.

Figures 6, 7:
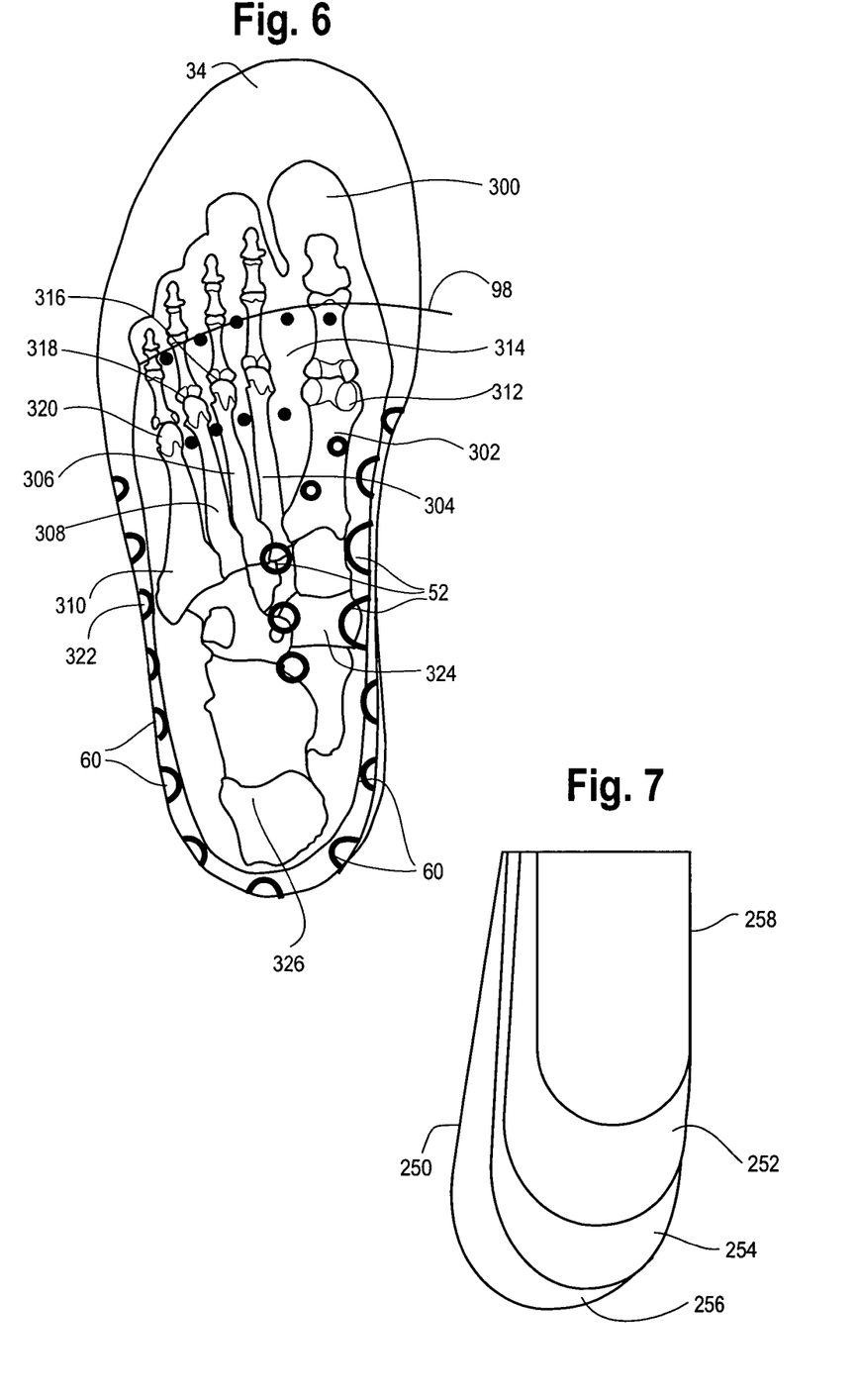
FIG. 6 is a view of the bones of the foot, positions of the foot and insole landmark for centering the orthopedic inserts of FIGS. 4A-4H.
FIG. 7 is a perspective view of a heel lift.

FIG. 6 is a diagram of a foot 300 showing the bones and areas of the foot 300 superimposed on the insole 10. The foot 300 has a suclus area 98 and a first metatarsal bone shaft 302, a second metatarsal shaft 304, a third metatarsal shaft 306, a fourth metatarsal shaft 308 and a fifth metatarsal shaft 310. The foot 300 has a first metatarsal head 312, a second metatarsal head 314, a third metatarsal head 316, a fourth metatarsal head 318, and a fifth metatarsal head 320. A styloid process bone 322 is the base of the fifth metatarsal shaft 310. The foot 300 also includes a navicular bone 324 and a Calcaneous or heel bone 326.

The forefoot dots 80-88 and midfoot dots 90-96 when connected allow the technicians to adjust for making a depression in the insole 10 for bruised or drop metatarsal bones 312-320 as shown in FIG. 6. Grinding or removing material from the beneath one or more metatarsal bones 312-320 in these positions offers relief of bruised metatarsals. The midfoot dots 90-96 indicate where the depression ends, just behind the metatarsal heads. This takes the weight off a bruised or painful area such as the metatarsal heads 312-320. The forefoot alignment dots 80-88 and flow domes 52 on the bottom surface 34 of the lower cradle 14 aid in placement of additions such as metatarsal rocker bars, forefoot varus (medial) or valgus (lateral) wedges or other correction devices added by a qualified, trained medical professional to further help balance and align the body as will be explained below. The correction devices have a hole pattern that aligns with the flow domes 52 and/or volume compensating domes 60. The additional correction devices are attachable by glue dots, or plastic tree rivets 68 for easy placement or removal with the bottom surface 34 of the lower cradle 14. They may also be permanently bonded with contact cement.

Figure 4A:
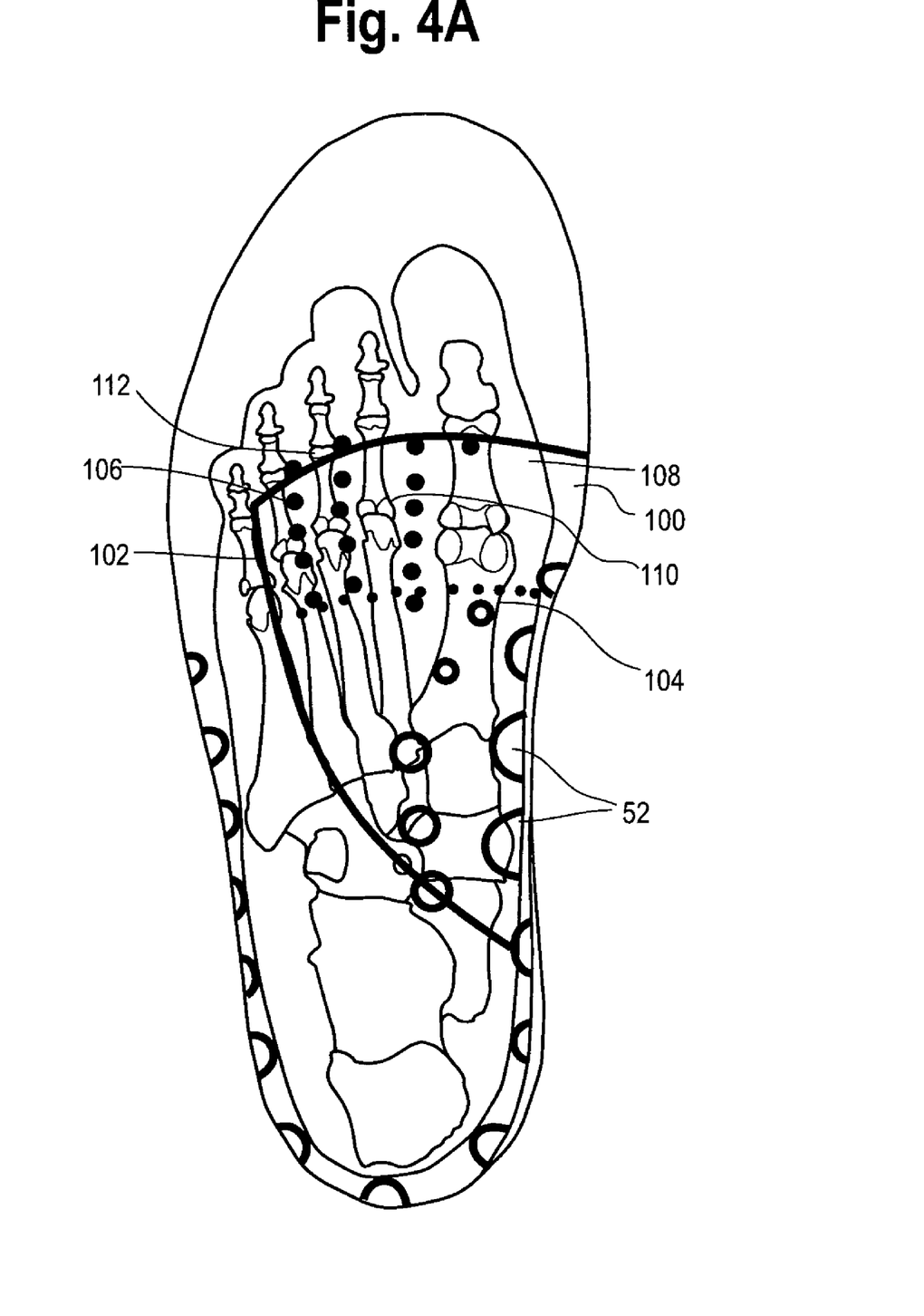
FIGS. 4A-4H show different orthopedic inserts and corrections which may be used with the insole in FIG. 1.

FIGS. 4A-H shows additional aspects of the insole 10 which allows the use of angled wedges or corrections. A medial wedge 100 is shown in FIG. 4A, which is used for balancing forefoot varus. Forefoot varus is the condition when the heel is in neutral or vertical and the first metatarsal is high angling towards the fifth metatarsal. The wedge 100 is preferably made in 3 and 6 degree versions. The wedge 100 has a bottom surface 102, which has a hole pattern 104 that aligns with the flow domes 52 of the insole 10. The medial wedge 100 has four U-shaped perforations 106, 108, 110 and 112 for the first, second, third and fourth metatarsal bones. When the perforation is torn and the EVA section removed, it creates a depression that allows the metatarsal head(s) 312-320 in FIG. 6 to "float" and removes excess pressure on the bone.

Figures 4B, 4C:
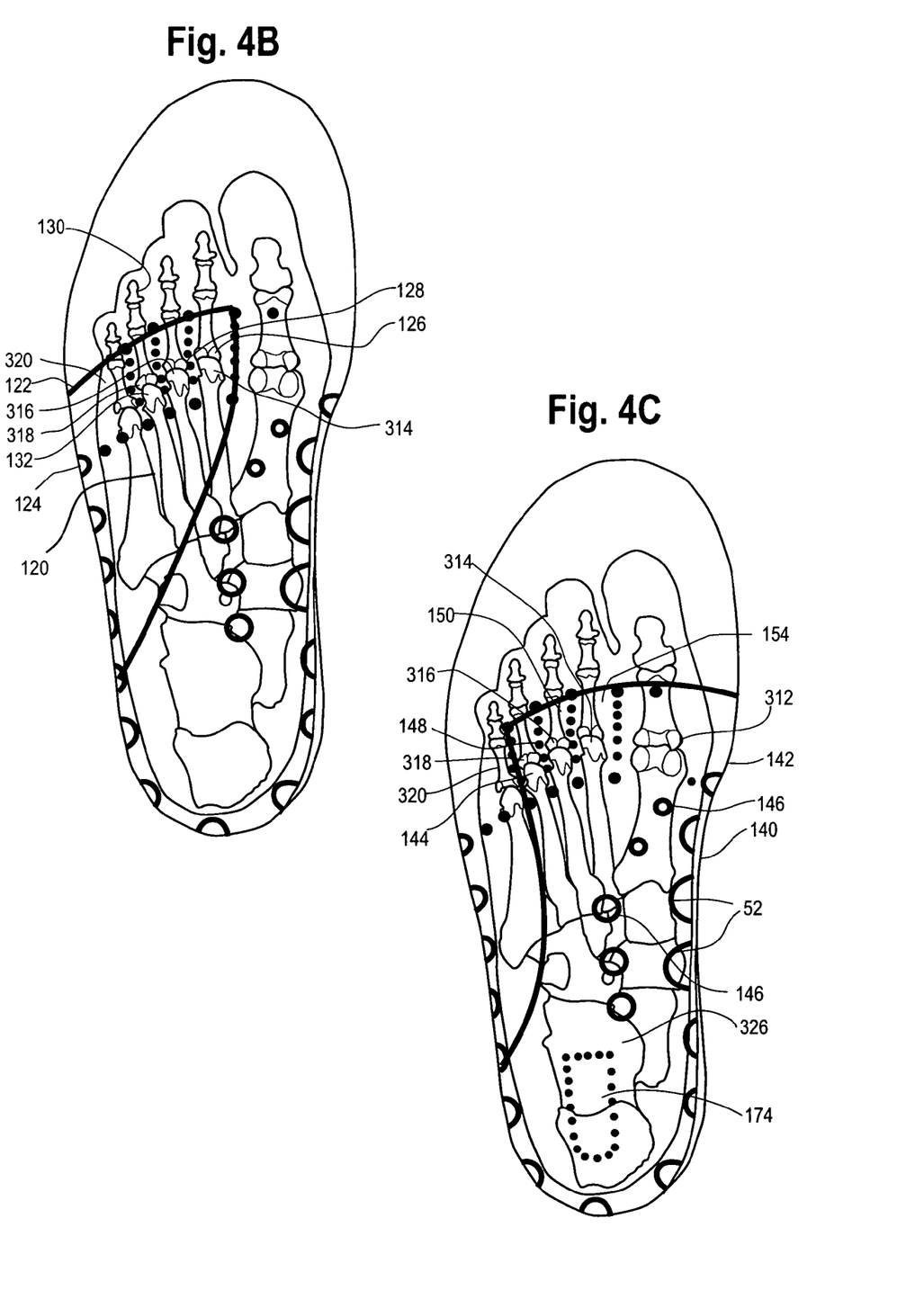

All the medial wedges style corrections are shown in FIGS. 4A and 4C and are designed with medial side thick beveled at an angle to the lateral side. All of the wedge corrections that extend under the forefoot in FIGS. 4A-4D have the forward edge aspect is beveled at an angle. FIG. 4I shows the creation of a rocker bottom 184 which will be explained below later.

FIG. 4B shows a lateral wedge 120 which is used for forefoot valgus alignment. Forefoot valgus is the condition when the heel is in neutral or vertical and the fifth metatarsal 320 is high angling down towards the first metatarsal 312, this gap must be filled to balance the foot. The wedge 120 has a bottom surface 122 which has a hole pattern 124 that aligns with the volume compensation domes 52 of the insole 10. The lateral wedge 120 has four U-shaped perforations 126, 128, 130 and 132 for the second metatarsal bone 314, third metatarsal bone 316, fourth metatarsal bone 318 and fifth metatarsal bone 320. This provides each metatarsal head with no tool adjustment for painful metatarsal bones. The lateral style wedge 120 is designed with a lateral side thick beveled thin at an angle to the medial side.

FIG. 4C shows a monopost medial wedge 140 of 3 or 6-degree angles which allows corrections for balancing a combination of forefoot and rear foot varus. With heel vertical the forefoot balances with the first metatarsal 312 high and fifth metatarsal low 320. This space must be filled to balance the foot. The monopost medial wedge 140 has a medial side 142, which is thick beveled at an angle to the lateral side 144 which is feather thin. A series of hole patterns 146 in the medial monopost wedge 140 aid in aligning the wedge 140 with the volume compensation domes 52 in the insole 10. The medial wedge 140 has four small U-shaped perforations 148, 150, 152 and 154 for the first metatarsal bone 312, second metatarsal bone 314, third metatarsal bone 316 and fourth metatarsal bone 318. All the corrections extending under the heel shown in FIGS. 4C, 4D, 4F, 4G and 4H have U-shaped perforations corresponding to the center of the heel 326 for no-tool relief of plantar fasciitis and heel spur syndromes. When the perforations are torn and the EVA section removed, it creates a depression to float or take pressure off the center of the heel 326 and the plantar fascitia tendon that attaches to it. The plantar fascia tendon begins under the center of the heel and attaches to the tip of the bit toe. Because of increased pressure under the heel a bruise can develop under the heel or along the plantar tendon. A depression under the center of the heel floats these areas under the heel bone relieving the pain.

Figure 4D:
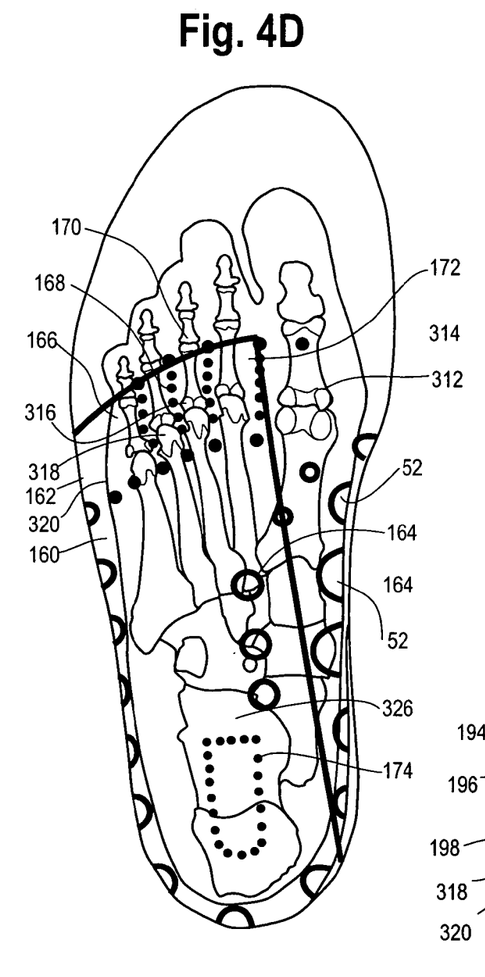

FIG. 4D shows a lateral monopost wedge 160, which addresses a combination of a forefoot and rear foot valgus. The lateral monopost wedge 160 has a lateral side 162, which is thick beveled at an angle to the feather thin to the lateral side 162. A series of hole patterns 164 in the lateral monopost wedge 160 aid in aligning the wedge 160 with the volume compensation domes 52 in the insole 10. The lateral monopost wedge 160 has four small U-shaped perforations 166, 168, 170, 172 for no tool depression for the second metatarsal bone 314, third metatarsal bone 316, fourth metatarsal bone 318 and fifth metatarsal bone 320. When the perforation is torn and the EVA section removed, it creates a depression that allows the metatarsal head(s) to "float" and removes excess pressure. A U-shaped perforation member 174 is surrounded by a plurality of perforations corresponding to the center of the heel 326 provides no-tool relief of plantar fasciitis and heel spurs syndromes. When the perforation member 174 is torn and the EVA section removed, it creates a depression to float or take pressure off the center of the heel 326 and the plantar fascia tendon that attaches to it.

Figure 4E:
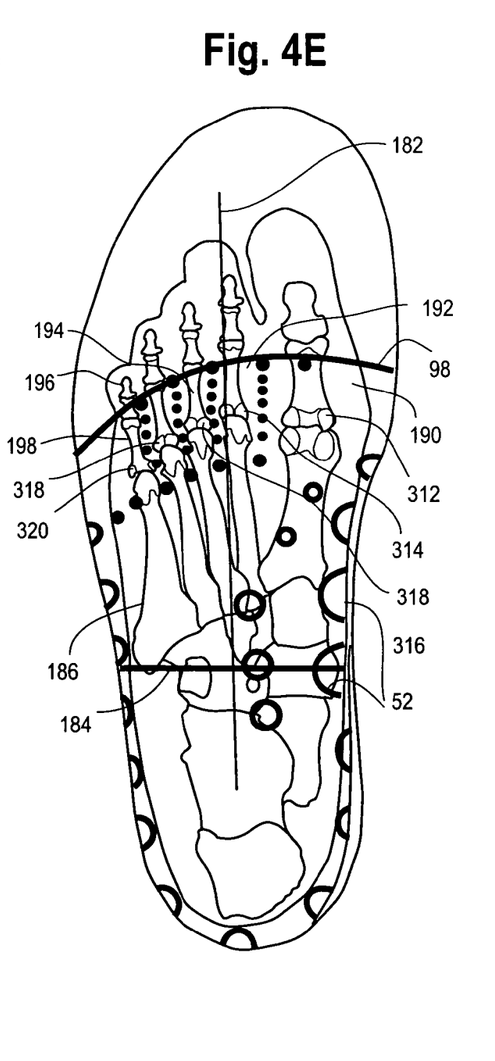
Figure 4F:
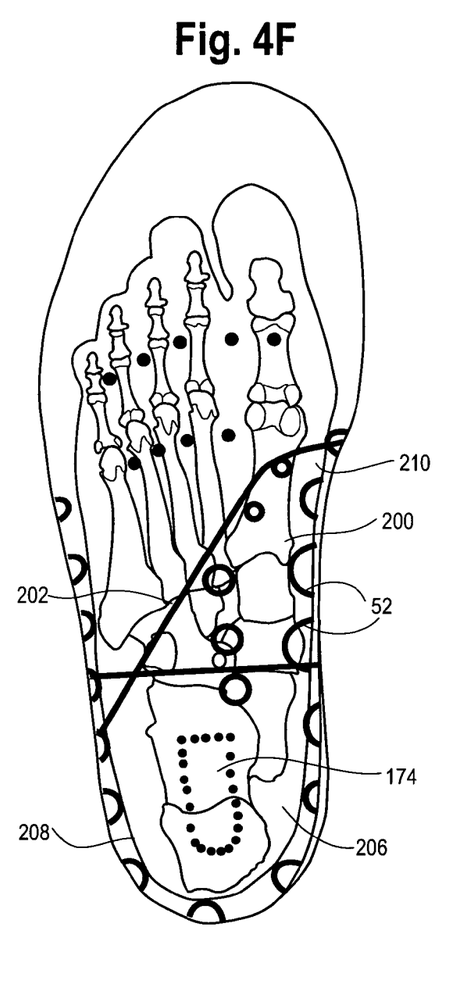
Figure 4G:
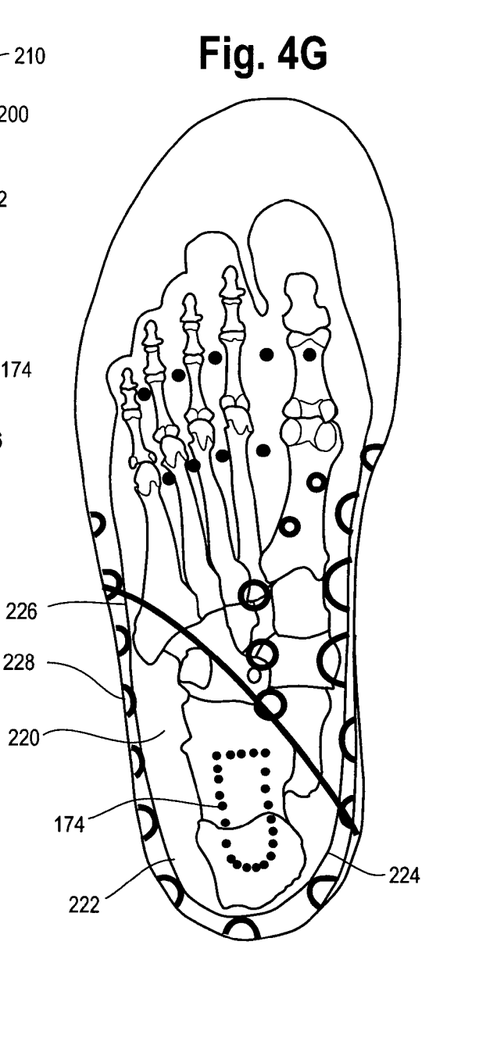
Figure 4H:
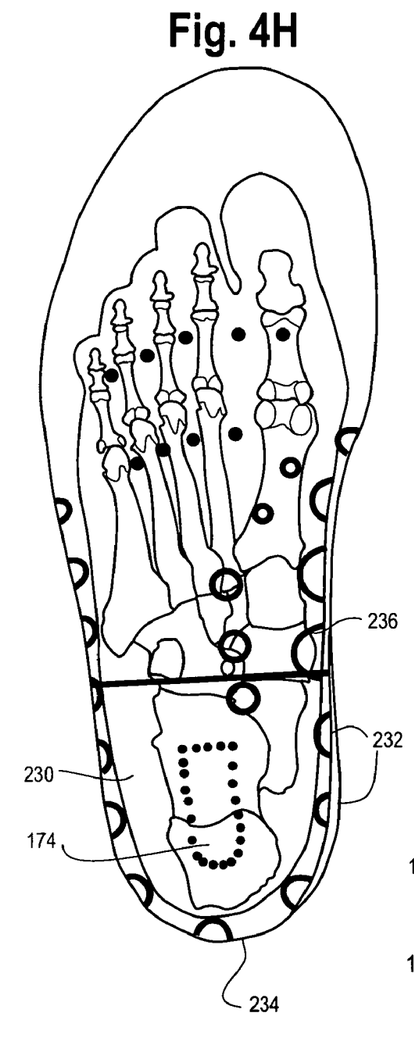
Figure 4I:
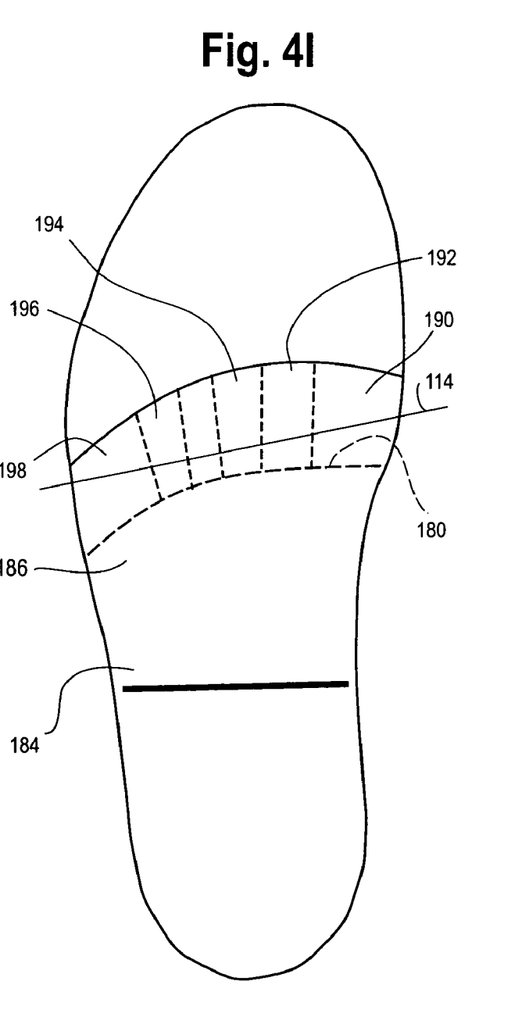
FIG. 4I is a view of the correction in FIG. 4E without the bones of the foot.
Figure 4J:
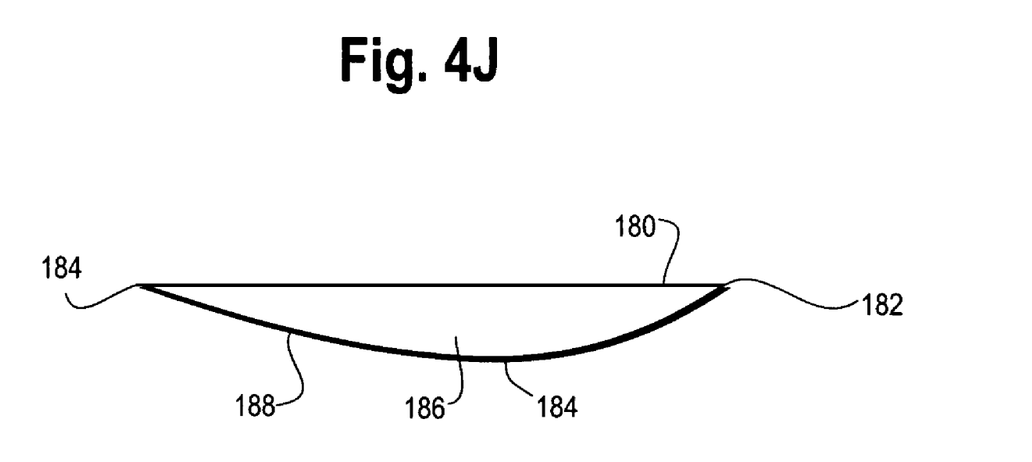
FIG. 4J is a cross-section of a rocker bar along the line 182 of the correction in FIG. 4E.

FIG. 4E shows a metatarsal rocker bar 180 which is compression or skive molded with a rounded rocker bottom as shown in FIG. 4J which is a cross section of FIG. 4E on a line 182 in FIG. 4E. The rocker bar 180 is designed to aid in toe and ankle flexion similar to a rocking chair for the shoe. The rocker bar 180 off-loads pressure under the toes and metatarsal heads. The rocker bar 180 is used when there is a limited toe flexion and/or ankle flexion. For maximum effectiveness, the rocker bar 180 starts at the sulcus 98 of the foot and is bevel rounded and rearward with a thickest point 186 ending ¼" to ⅜" behind the metatarsal heads 312-320. The rocker bar 180 includes an arm 188 which is angled rearward and is beveled to a feather edge. The series of flow domes 52 and volume compensating domes 60 in the insole 10 aid in the placement of the rocker bar 180. Metatarsal bars are another effective means for taking pressure off the metatarsal heads when there are no forefoot alignment problems such as a forefoot varus or valgus conditions. The metatarsal rocker bar 180 is preferably made of EVA and can be skive molded when using Poron. The metatarsal rocker bar has five U-shaped perforations 190, 192, 194 196 and 198 for easy tear, no tool correction of dropped or bruised metatarsals 312-320 or relief for painful corns and calloused. When the perforation is torn and the EVA section removed, it creates a depression that allows the metatarsal head(s) 312-320 to "float" and removes excess pressure.

Figure 4K:
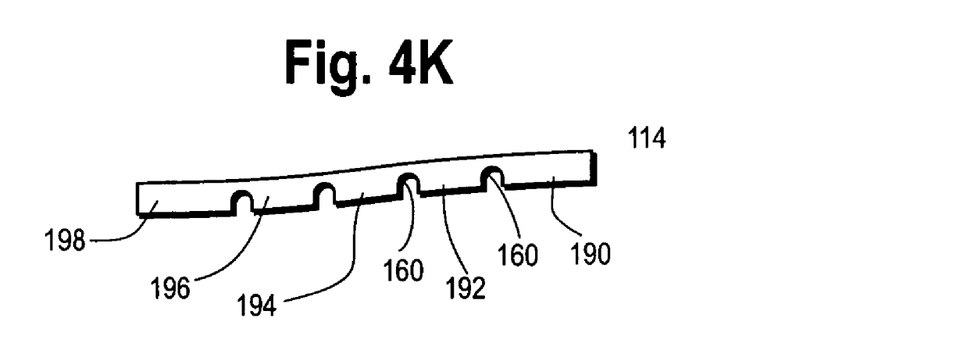
FIG. 4K is a cross-section of the rocker bar along line 114 in FIG. 4I.

FIG. 4K shows a cross-section of the metatarsal rocker bar 180 in FIGS. 4E and 4I at a line 114 in FIG. 4I. The perforations 190-198 used for no-tool relief of bony problems each have a channel 160 which is ½" to ¼" compression molded into the bottom surface extending down so the material is paper-thin. The channels 160 are preferably ⅛" to ¼" wide to create a bevel so when a perforation is torn it creates a smooth transition for the cutout area. One or more (cut-outs) of the no-tool tear perforation lines can be utilized at the same time. The perforations may optionally have the channel molded into the bottom. All corrections described above may include the channel 160 and/or the perforations.

FIG. 4F shows a medial wedge 200 which is used for corrections for balancing rear foot varus. The thickest point of the medial wedge 200 is at a heel medial aspect 206 and is beveled to a feather edge 208 laterally as well as forward to the front medial edge 210. The medial wedge 200 may be made in 3 and 6-degree angles preferably. The medial wedge 200 has a hole pattern 202 which aligns with the flow domes 52. The medial wedge 200 has a horseshoe-shaped perforation member 174 in the center for no-tool relief of plantar fasciitis and heel spurs syndromes. When the perforation is torn and the EVA section removed, it creates a depression to float or take pressure off the heel spur and plantar fascitia tendon relieving plantar fasciitis.

FIG. 4G shows a lateral wedge 220 for forefoot valgus imbalances. The thickest point of the lateral wedge 220 is at the heel's lateral aspect 222 and is beveled to a feather edge 224 medially as well as forward to a front lateral edge 226. The lateral wedge 220 may be made in 3 and 6-degree angles preferably. The lateral wedge 220 has a hole pattern 228, which aligns with the volume compensating domes 52 in the insole 10. The lateral wedge 200 has a horseshoe-shaped perforation member 174 in the center for easy removal for heel spurs and other disorders.

FIG. 4H shows a heel lift 230 for calf cramps, Achilles Tendonitis or for lifting a short leg for which the lift 230 may be installed at varying heights. A hole pattern aligns the heel lift 230 with the volume compensating domes 60 of the insole 10. The heel lift 230 is thickest at a rear end 234 and beveled to a featheredge 236 forward. The lift 230 has a horseshoe-shaped perforation member 174 in the center for no-tool relief of plantar fasciitis and heel spurs. When the perforation member is torn and the piece removed, a depression is formed to float or take pressure of the center of the heel for alleviating a painful heel spur and plantar fasciitis. The plantar fascia tendon begins under the center of the heel and attaches to the tip of the big toe. Because of increased pressure under the heel a bruise can develop under the heel or along the plantar tendon. A depression under the center of the heel floats these areas under the heel bone relieving the pain.

FIG. 7 shows an alternate style of a heel lift 250. The heel lift 250 has tear perforation lines 252, 254 and 256 to make the heel lift 250 shorter and narrower for use in smaller size footwear. The heel lift 250 may have an optional cutout to line up with the flow domes 52 and the contour dimples 60 of the insole 10. The heel lift 250 is preferably $3/8$" thick and $3\frac{3}{4}$" long at a large size which is indicated by the line 256 and $1/4$" thick and 3" long for a medium size line 254 and $3/16$" thick at the heel and $2\frac{1}{2}$" long for a small size line 252 which yields a 6-12 degree lift. All the heel lifts noted above are thick at the back end and beveled to a featheredge at the front line 258.

Figure 5:
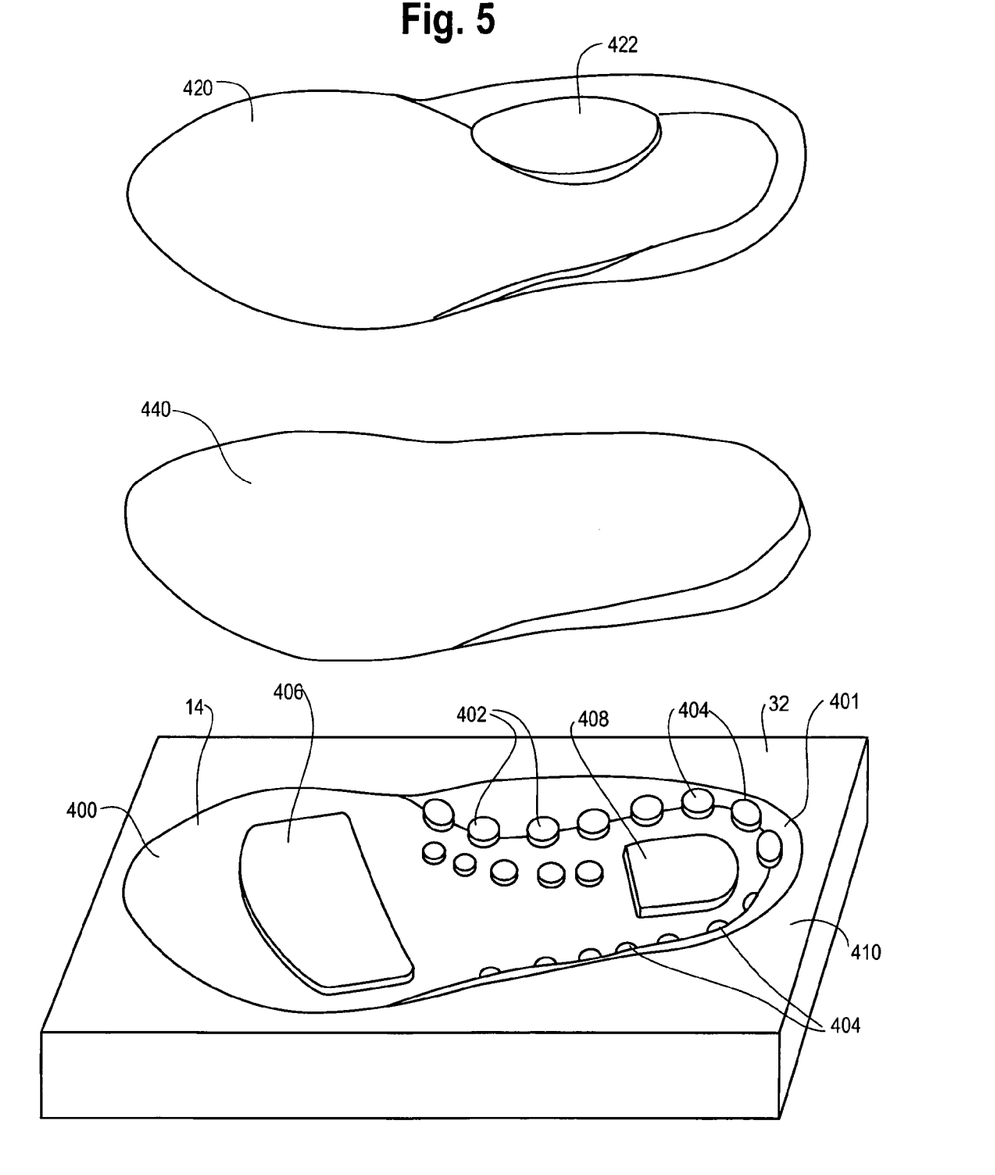
FIG. 5 is an exploded perspective view of the compression molds used to manufacture the moldable insole in FIG. 1.

A three-part compression mold is used to fabricate the insole 10 as shown in FIG. 5. A female mold 400 is employed for molding the core of the shell 32, which includes the insole lower cradle 14. The mold 400 has a base 410 with a series of flow dome dimple molds 402 and a series of volume compensating dimples molds 404. The mold 400 also has a forefront platform 406 and a rear raised platform 408 to form the recesses 56 and 58 for Poron plugs 62 and 64. Two corresponding male molds 420 and 440 which mate with the female mold 400 are also used. The first compression male mold 420 forms the top cradle shell and forms an arch recess mold 422 which forms the arch area 66 where the gel layer 16 sits. A second male mold 440 is used for finishing the top softer cradle 12 with fabric cover. This gives the insole 10 its finished look.

With a three-part compression process, the firm lower cradle 14 is formed first with the mold 400. Then the softer top material is heated and compression molded in a second step. This second step in the molding process provides the ability to maintain the soft comfortable, shock-absorbing feel of the upper cradle 12. The result is the upper cradle 12 functions differently than the lower cradle 14. The process enables the upper and lower cradles 12 and 14 to be made of varying densities of material for different sports, dress shoes, walking or the diabetic foot. The insole can be full length, $7/8$ (sulcus) length or $3/4$ (behind metatarsal heads) in length.

The preferred material for the top cover 20 of the upper cradle 12 must be soft, moldable and take a permanent set. For example, the material most commonly used for a diabetic foot is Plastazote. Plastazote is an open-cell foam that prevents the skin from breaking down and ulcerating. The two-step process described above makes possible a custom molded diabetic insole that is economic because it eliminates the need for a plaster cast or direct molding of an insert with a patient's foot. The present method improves on plaster cast or direct molding which require an insert to be made from flat pieces of material which then require hours of working time to grind down the excess bulk and fit into the footwear.

The process of compression molding one pair of insoles that are formed at the same time will now be explained with reference to FIG. 5. The lower cradle 14 is formed by resting the female mold 400 on a platform. The first male mold 420 is locked into place on a hydraulic arm. A half-inch thick square piece of EVA, pre-coated with heat-activated cement, is heated in an oven (250-350 F for 3-5 minutes). When warm, the EVA material is placed over the female mold 400. The hydraulic arm with the first male mold 420 in place is a lowered compressing the EVA material with over 5 tons of pressure. This forms a blocker, which is a pair of lower cradles 14 that are attached to each other. The blocker is flash cooled and removed. The flow domes 52 and contouring dimples 60 are then perforated via a perforation die. The blocker is then placed back into the female mold 400. The gel layer 16 is placed into the premolded recess 36 on the top portion arch area 48 of the lower cradle 14. The first male mold 420 is removed and replaced with the second male mold 440. A $1/4$-in. EVA material forms the upper cradle 12 and the ETC fabric backing 20 is coated with heat activated cement and attached. The assembly is then placed in the oven (250-300F for $1/2$ to $2\frac{1}{2}$ minutes). The EVA material is heated until soft, then placed over the blocker and compression molded forming the insole 10. The blocker is flash cooled for one minute and removed from the mold. Using a perimeter die, the insole is die cut to reveal the finished shape of the insole and a pair of insoles. The Poron shock platforms 62 and 64 are then glued into place.

After compression molding, the core becomes much stiffer and denser due to compressing the EVA to $1/8$-in. thick in the forefoot area 46. This makes the insole torsionally rigid preventing twisting or rocking with excessive side-to-side motion. However, the insole 10 remains firm but resilient in the arch and heel area.

During compression molding the forefoot depression 58 and heel area depression 56 are compressed paper-thin with a recess created for the placement of the Poron platforms 62 and 64. The thinned area makes it possible for the Poron plugs to be felt through the top layer, adding cushioning under the heel and forefoot for supplemental shock absorption. On the bottom surface of the lower cradle 14, the trim lines 70 and 72 are compression molded in for easy fitting.

The present insole 10 is compatible with all arch heights as it auto-adapts when heated. With the addition of the corrective wedges described above, the insole can solve 95% of most medical foot problems. The insole 10 will assist a the normal foot (7% of population), the pronated foot (90%) and the high-supinated foot (3%). The insole 10 is built with a very deep, neutral heel (vertical heel cup), which holds the heel in a neutral position reducing pronation. When the arch is molded, it yields a uniform contour fit from behind the first metatarsal to the base of the heel. This contour fit increases shock absorption and reduces pronation during walking or sports. Corrections, additional wedges or pads may be added to the bottom of the device to increase or decrease pronation, adjust for dropped metatarsal bones and heel spurs, or create a rocker bottom forefoot. The deep heel cup supports the whole foot helping to prevent pronation while keeping the heel vertical. Compression molding is used for fabricated the insole 10 as it yields a stronger, more torsionally rigid and stable device than injection molding or skive molding.

Figure 8:
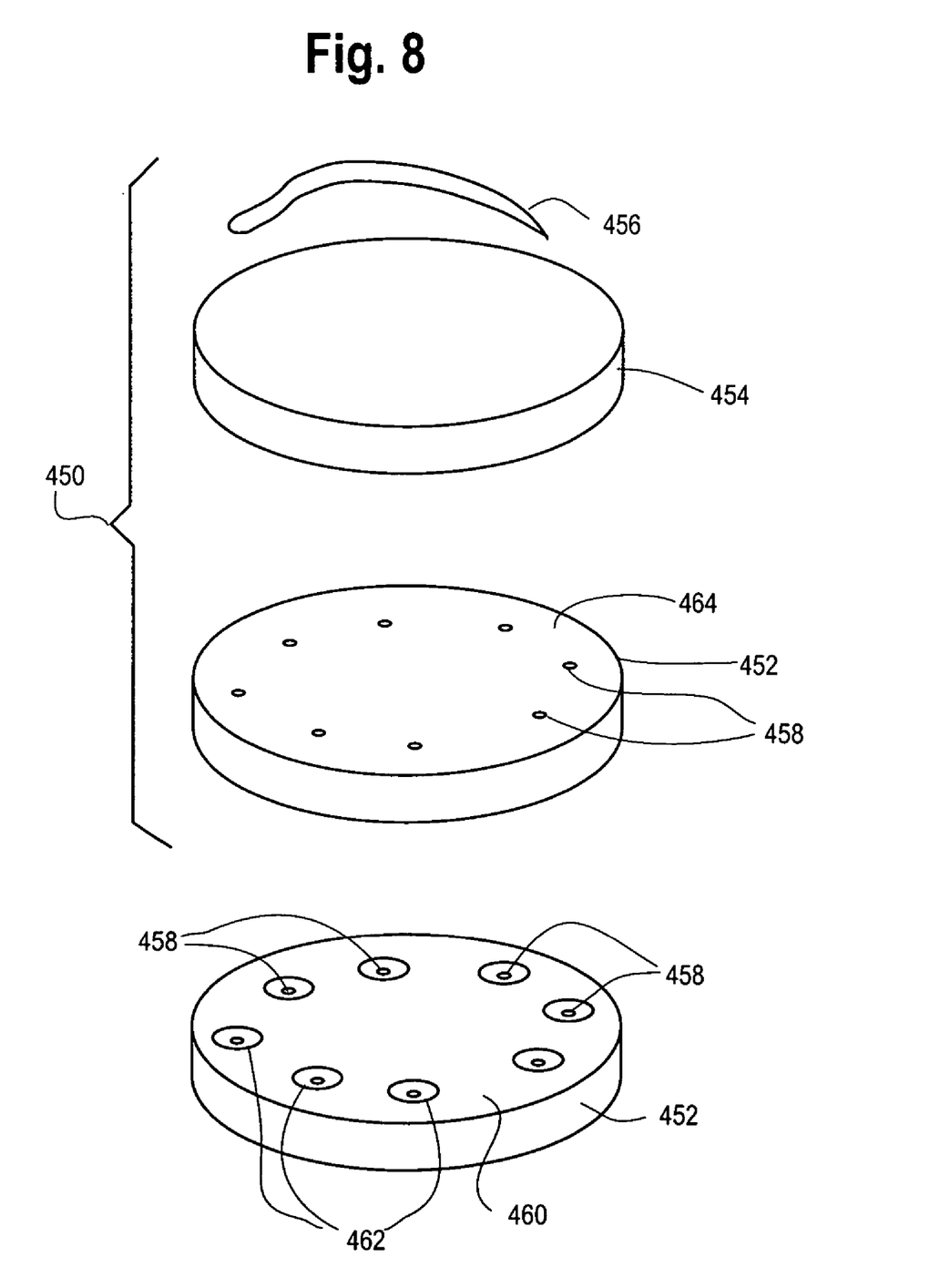
FIG. 8 is a perspective view of a flat, user adjustable insert according to the present invention.

Other aspects of the invention are custom molded ankle, knee, hand and back supports which may be molded easily without error. The gel and EVA pads allow the brace to be custom tailored to wide, normal or narrow ankles, knees, hand elbow and the foot. FIG. 8 shows a flat oval insert 450 that can be used as custom padding in a knee brace, back or ankle brace, which is still user moldable. The oval insert 450 has a bottom layer 452 which is preferably fabricated from EVA, a gel layer 454, a top film 456 which is preferably a 3mm polypropylene plastic. The oval insert 450 includes an undersurface 460 and an opposite top surface 464. The insert bottom layer 452 can be flat with the gel layer 454 resting on the top. The top surface 464 of the bottom of the insert 452 has flow hole bores 458 thru the EVA padding. The underside 460 of the insert 452 has a flow dome 462 and a flow hole 458 for excess gel to exhaust through, yielding a custom fit. The moldable insert 450 could be a square or rounded shape ¼" to ⅜" thick with the gel layer 454 being ⅛" to ½" thick. The EVA material preferably is 35 D after compression molding and 25 D before molding. The flow holes 458 are bored through the lower pad 452 to contact the gel layer 454. The flow hole 458 allows excess gel to exhaust into the flow domes 462. The insert 450 could be flat, oval, round shape. The bottom 460 and/or top 464 of the EVA layer maybe molded with a concave or convex surfaces which are mated to the product so that the insert 450 will be used such as a foot insert, or ankle, knee and back braces.

It will be apparent to those skilled in the art that various modifications and variations can be made in the method and system of the present invention without departing from the spirit or scope of the invention. Thus, the present invention is not limited by the foregoing descriptions but is intended to cover all modifications and variations that come within the scope of the spirit of the invention and the claims that follow.

What is claimed is:

1. An insole for insertion in footwear, the insole comprising:
    an upper cradle, having an upper surface for contact with a foot and a lower interlocking surface;
    a lower cradle, having an upper surface defining an arch depression and a lower surface defining a flow dome, the lower cradle defining a flow hole fluidly communicating the flow dome with the arch depression, said lower surface of said lower cradle and a surface of the footwear defining said flow dome when a user stands in the footwear; and
    a gel layer located in the arch depression, the gel layer being moldable via heating, said flow dome having a size to serve as a reservoir for an excess of said gel layer.

2. The insole of claim 1 wherein the upper cradle is fabricated from a low density EVA material to provide cushioning and the lower cradle is fabricated from a higher density EVA to provide support.

3. The insole of claim 1 wherein the upper surface of the upper cradle includes a top layer fabricated from ETC material.

4. The insole of claim 1 wherein the lower surface of the lower cradle has a heel depression and a forefront depression and a heel pad is installed in the heel depression and a forefront pad is installed in the forefront depression.

5. The insole of claim 4 wherein the pads are fabricated from Poron.

6. The insole of claim 1 further comprising a corrective wedge having a surface with stubs to match the lower surface of the lower cradle.

7. The insole of claim 6, wherein the corrective wedge is a medial wedge.

8. The insole of claim 6, wherein the corrective wedge is a lateral wedge.

9. The insole of claim 6, wherein the corrective wedge is a metatarsal rocker bar wedge.

10. The insole of claim 1 wherein the lower surface includes a perforation member surrounded by a plurality of perforations for adjustment of heel spurs.

11. The insole of claim 1 further comprising a corrective heel lift having a length and width corresponding to the insole.

12. The insole of claim 11 wherein the heel lift has a corrective adjustment perforation corresponding to a predetermined length and width.

13. The insole of claim 1 further comprising a series of contour dimples on the lower surface for adjustment of different heel widths.

14. An orthopedic device for contouring a force applying interface between a user and a surface on an external object, the device comprising:
    a first cradle having an outer surface for contact with a surface of the user, said first cradle having an inner surface arranged diametrically opposite said outer surface;
    a second cradle connected to said first cradle, said second cradle having an inner surface facing said inner surface of said first cradle, said inner surface of said first cradle and said inner surface of said second cradle defining a gel cavity between said first and second cradles, said second cradle having an outer surface arranged diametrically opposite said inner surface of said second cradle, said outer surface of said second cradle being arranged for contact with the surface of the external object, said outer surface of said second cradle defining a flow dome, said second cradle defining a flow hole forming a passage between said gel cavity and said flow dome, said outer surface of said second cradle and the surface of the external object defining said flow dome;
    a gel material arranged in said gel cavity, said gel material being moldable via heating.

15. An orthopedic device in accordance with claim 14, wherein:
    said outer surface of said second cradle and the surface of the external object define said flow dome during the force applying interface.

16. An orthopedic device in accordance with claim 14, wherein:
    said flow dome has a size to serve as a reservoir for excess said gel material.

17. An orthopedic device in accordance with claim 14, wherein:
    said outer surface of said second cradle defines a plurality of said flow domes.

18. An orthopedic device in accordance with claim 14, wherein:
    said gel material has a temperature dependent viscosity;
    the orthopedic device has a first temperature range for normal operation, and a second temperature range for adjustments;
    said second temperature range, said viscosity of said gel material at said second temperature range, and said flow hole being arranged to have said gel material flow from said gel cavity through said flow hole and into said flow dome to adjust the interface between the user and the surface of the external object when the orthopedic device is at said second temperature range;
    said first temperature range, said viscosity of said gel material at said first temperature range, and said flow hole being arranged to have said gel material transfer force between the user and the surface of the external object when the orthopedic device is at said first temperature range.

19. An orthopedic device in accordance with claim 14, wherein:
   said gel material has an optimal hardness greater than 16 on a Type "O" scale durometer and less than 45 on a Type "A" scale durometer and can be softened to a moldable hardness of less than 2 by heating at 60 degrees Celsius.

20. An orthopedic device in accordance with claim 14, wherein:
   the surface of the user is a foot, and the external object is footwear.

21. An orthopedic device in accordance with claim 20, wherein:
   said outer surface of said second cradle and a surface of the footwear define said flow dome when the user stands in the footwear.

22. An orthopedic device in accordance with claim 21, wherein:
   said flow dome has a size to serve as a reservoir for excess said gel material;
   said outer surface of said second cradle defines a plurality of said flow domes;
   said gel material has a temperature dependent viscosity;
   the orthopedic device has a first temperature range for normal operation, and a second temperature range for adjustments;
   said second temperature range, said viscosity of said gel material at said second temperature range, and said flow hole being arranged to have said gel material flow from said gel cavity through said flow hole and into said flow dome to adjust the interface between the user and the surface of the external object when the orthopedic device is at said second temperature range;
   said first temperature range, said viscosity of said gel material at said first temperature range, and said flow hole being arranged to have said gel material transfer force between the user and the surface of the external object when the orthopedic device is at said first temperature range;
   said gel material has an optimal hardness greater than 16 on a Type "O" scale durometer and less than 45 on a Type "A" scale durometer and can be softened to a moldable hardness of less than 2 by heating at 60 degrees Celsius for a period of greater than 3 minutes and less than 10 minutes.

23. An orthopedic device for contouring a force applying interface between a user and a surface on an external object, the device comprising:
   a first cradle having an outer surface for contact with a surface of the user, said first cradle having an inner surface arranged diametrically opposite said outer surface, the surface of the user being a foot;
   a second cradle connected to said first cradle, said second cradle having an inner surface facing said inner surface of said first cradle, said inner surface of said first cradle and said inner surface of said second cradle defining a gel cavity between said first and second cradles, said second cradle having an outer surface arranged diametrically opposite said inner surface of said second cradle, said outer surface of said second cradle being arranged for contact with the surface of the external object, said outer surface of said second cradle defining a flow dome, said second cradle defining a flow hole forming a passage between said gel cavity and said flow dome, the external object being footwear, said outer surface of said second cradle and a surface of the footwear define said flow dome when the user stands in the footwear;
   a gel material arranged in said gel cavity, said gel material being moldable via heating.

* * * * *